United States Patent
Scotto et al.

(10) Patent No.: US 11,059,793 B2
(45) Date of Patent: Jul. 13, 2021

(54) PROCESS FOR MELAMINE PURIFICATION

(71) Applicant: Casale SA, Lugano (CH)

(72) Inventors: Andrea Scotto, Breganzona (CH); Simone Gamba, Pagazzano (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 16/318,736

(22) PCT Filed: Jun. 21, 2017

(86) PCT No.: PCT/EP2017/065187
§ 371 (c)(1),
(2) Date: Jan. 18, 2019

(87) PCT Pub. No.: WO2018/015093
PCT Pub. Date: Jan. 25, 2018

(65) Prior Publication Data
US 2019/0152928 A1 May 23, 2019

(30) Foreign Application Priority Data

Jul. 22, 2016 (EP) ..................................... 16180820

(51) Int. Cl.
*C07D 251/62* (2006.01)
*C07D 251/60* (2006.01)

(52) U.S. Cl.
CPC ......... *C07D 251/62* (2013.01); *C07D 251/60* (2013.01)

(58) Field of Classification Search
CPC ............................ C07D 251/60; C07D 251/62
USPC .................................................. 544/203, 201
See application file for complete search history.

(56) References Cited

U.S. PATENT DOCUMENTS

| 7,176,309 B2 | 2/2007 | Schroder et al. |
| 7,445,722 B2 | 11/2008 | Ruech et al. |
| 7,723,516 B2 | 5/2010 | Toplack et al. |
| 7,741,481 B2 | 6/2010 | Ruech |
| 9,206,140 B2 * | 12/2015 | Schadt ................. C07D 251/60 |
| 2011/0003990 A1 | 1/2011 | Sioli |

FOREIGN PATENT DOCUMENTS

| EP | 0 212 240 A1 | 3/1987 |
| WO | 2011/042532 A1 | 4/2011 |

OTHER PUBLICATIONS

International Search Report issued in connection with PCT/EP2017/065187.
International Preliminary Report on Patentability issued in connection with PCT/EP2017/065187.
Simon, Alexander et al., "Sodium Hydroxide Production from Sodium Carbonate and Bicarbonate Solutions Using Membrane Electrolysis: A Feasibility Study," Separation and Purification Technology, vol. 127, Feb. 28, 2014, pp. 70-76.

\* cited by examiner

*Primary Examiner* — Tracy Vivlemore
*Assistant Examiner* — Ebenezer O Sackey
(74) *Attorney, Agent, or Firm* — Akerman LLP

(57) ABSTRACT

A process for the purification of a melamine melt (5) containing melamine and by-products, comprising the steps of: (a1) quenching of said melamine melt; (a2) decomposition of by-products with alkali, providing an alkaline aqueous solution of melamine (26); (b) stripping of said alkaline aqueous solution of melamine (26); (c) crystallization of melamine with a first alkali-containing solution (6b) and separation of solid melamine (7) from a mother liquor (8); (d) treatment of said mother liquor, providing a waste water stream (11) containing carbonates; (e) decomposition of at least part of the carbonates contained in said waste water stream (11) into carbon dioxide and alkali, providing a second alkali-containing aqueous solution (30); (f) recycle of at least part of said alkali-containing aqueous solution (30) to at least one of said steps (a1), (a2) and (c).

10 Claims, 6 Drawing Sheets

PROCESS FOR MELAMINE PURIFICATION

This application is a national phase of PCT/EP2017/065187, filed Jun. 21, 2017, and claims priority to EP 16180820.9, filed Jul. 22, 2016, the entire contents of both of which are hereby incorporated by reference.

FIELD OF APPLICATION

The invention relates to the field of melamine production from urea. In particular, the invention relates to the purification of a melamine melt obtained from a high pressure non-catalytic process.

PRIOR ART

The processes for the synthesis of melamine from urea comprise low pressure catalytic processes and high pressure non-catalytic processes. These processes are well-known in the art. The high pressure non-catalytic processes, in particular, operate at a pressure typically above 7 MPa and temperature of 300 to 450° C.

Both low-pressure and high-pressure processes include basically the steps of: synthesis of a melamine melt from urea; purification of the melamine melt; off-gas treatment.

According to the technology mainly used in the high pressure non-catalytic melamine processes, the conversion of urea into the melamine melt also generates off-gas mainly consisting of ammonia and carbon dioxide and a number of by-products mainly comprising OATs and polycondensates. Carbon dioxide is typically separated prior to the melamine melt purification, which is indeed aimed to remove such by-products, the unconverted urea and dissolved ammonia. The purification of the melamine melt generally takes place via dissolution of the melamine melt and subsequent crystallization of solid melamine. Examples of said melamine purification processes are disclosed in U.S. Pat. Nos. 7,176,309 and 7,741,481.

The melamine melt is quenched in an alkali-containing aqueous solution wherein the melamine, the unconverted urea and the by-products are dissolved, resulting in an alkaline aqueous solution of melamine. The quenching with said alkali-containing solution results in an increase of the pH which is desirable for a more rapid hydrolysis of the by-products.

Said alkali-containing aqueous solution may comprise, for example, sodium hydroxide (NaOH) or potassium hydroxide (KOH).

The resulting alkaline solution of melamine is fed to a crystallizer, where crystallized solid melamine is separated from an alkali-containing aqueous solution also termed mother liquor.

Said mother liquor contains residual amounts of by-products and, according to the prior art, is treated in a waste water treatment unit as disclosed for example in U.S. Pat. Nos. 7,445,722 and 7,723,516.

In the above waste water treatment unit, carbonates and bicarbonates are generated by reaction between alkali (e.g. NaOH or KOH) contained in the mother liquor and the carbon dioxide released by the by-product hydrolysis. Accordingly, the waste water treatment unit discharges a waste water stream containing carbonates and bicarbonates.

Even though said waste stream is not toxic, its discharge could be an issue when environmental regulations pose restrictions on the effluent salinity.

In addition, the discharge of said waste stream implies an alkali make-up and a water make-up to the melamine process, which entail elevated costs related to the provision of fresh alkali and fresh water.

SUMMARY OF THE INVENTION

The purpose of the invention is to solve the above shortcomings of the prior art.

Said purpose is achieved with a process for the purification of a melamine melt containing melamine and by-products and obtained from a high pressure non-catalytic synthesis process, said process comprising the steps of:

(a1) quenching of said melamine melt;

(a2) decomposition with alkali of at least part of said by-products, providing an alkaline aqueous solution of melamine;

(b) stripping of said alkaline aqueous solution of melamine, resulting in a stripped melamine solution;

(c) crystallization of melamine from said stripped melamine solution with a first alkali-containing aqueous solution and separation of melamine from a mother liquor;

(d) treatment of at least part of said mother liquor, providing an aqueous solution containing carbonates;

(e) decomposition of at least part of the carbonates contained in said aqueous solution into carbon dioxide and alkali, providing a second alkali-containing aqueous solution and a water stream;

(f) recycle of at least part of said second alkali-containing aqueous solution to at least one of said steps (a1), (a2) and (c).

According to some embodiments, said second alkali-containing aqueous solution is recycled to two of said steps (a1), (a2) and (c), or to all of them.

Preferably, said step (e) of decomposition is performed by means of an electrolysis process of the aqueous solution containing carbonates provided by the step (d) of treatment. In most cases, said aqueous solution also contains bicarbonates. For ease of description, reference is made below to an aqueous solution containing carbonates and bicarbonates.

Preferably, the aqueous solution provided by said step (d) is subjected to an ultrafiltration step before being sent to said electrolysis process, in order to remove suspended solids which may be present therein and would negatively affect the electrolysis process.

According to some embodiments of the invention, said second alkali-containing aqueous solution provided by the decomposition step (e) is at least partially subjected to a concentration step before being recycled to at least one of said steps (a1), (a2) and (c).

The term "high pressure non-catalytic synthesis process" denotes a non-catalytic process for the synthesis of melamine operating at a pressure which is preferably equal to or greater than 7 MPa.

The by-products contained in the melamine melt comprise for example OATs (i.e. ammeline, ammelide) and melamine poly-condensates (i.e. melam, melem, melon). Typically, said melamine melt also contains dissolved ammonia and unconverted urea. The term of "impurities" will be used to denote said by-products and also the unconverted urea and dissolved ammonia.

According to different embodiments, said step (a1) of quenching can be carried out with water ("water quenching") or with alkali ("alkaline quenching").

According to an embodiment of the invention, in the case of alkaline quenching said second alkali-containing aqueous solution is recycled at least in part to said step (a1) of quenching to act as a quenching agent.

The process of decomposition (a2), also referred to as hydrolysis, proceeds more rapidly the higher the pH in the solution. A pH comprised in the range 9 to 12 is preferred; to this purpose said step (a2) of decomposition is preferably performed in the presence of an aqueous solution containing potassium hydroxide (KOH) or sodium hydroxide (NaOH).

When water quenching is performed, said aqueous solution of KOH or NaOH is, according to various embodiments, at least partially provided by a portion of the mother liquor obtained from said crystallization step (c) and/or at least a portion of the second alkali-containing solution from the decomposition step (e). According to this embodiment, the steps of quenching (a1) and decomposition (a2) are preferably carried out in two separate equipment, namely a quencher and a decomposer, respectively.

When alkaline quenching is performed, a third alkali-containing solution is fed as a quenching medium to said step (a1) of quenching and an alkaline aqueous solution containing melamine and impurities is obtained. Said third alkali-containing solution is preferably an aqueous solution of KOH or NaOH.

According to said embodiment of alkaline quenching, the alkali (e.g. KOH or NaOH) in the presence of which the step (a2) of decomposition is performed are preferably at least partially provided by the alkaline aqueous solution obtained from said step (a1) of quenching, which contains alkali besides melamine and impurities. More preferably, said alkali are entirely provided by said alkaline solution and no further alkali is supplied.

Preferably, said third alkali-containing aqueous solution comprises a portion of the mother liquor provided from said step (c) of crystallization.

According to some embodiments, said third alkali-containing aqueous solution comprises at least a portion of the second alkali-containing solution from the decomposition step (e).

According to other embodiments, at least a portion of said second alkali-containing aqueous solution and a portion of said mother liquor are mixed to form the third alkali-containing aqueous solution or a portion thereof.

The alkaline quenching and the decomposition step can be carried out in the same equipment, but are preferably carried out in a separate quencher and a separate decomposer. Generally, the decomposition of melamine poly-condensates already starts in the quencher due to the introduction of an alkali-containing solution and the related pH increase, and advances in the decomposer wherein the alkaline effluent of the quencher resides for a proper time until hydrolysis is complete or substantially complete.

During the step (b) of stripping, ammonia is at least partially stripped from the alkaline aqueous solution of melamine, providing the above mentioned stripped solution and an aqueous solution of ammonia. Steam is preferably used as stripping medium. Preferably, said aqueous solution of ammonia is at least partially subjected to said step (d) of the treatment of mother liquor.

The resultant ammonia-depleted stripped solution and said first alkali-containing aqueous solution are subjected to crystallization, thereby melamine is crystallized out and separated from melamine mother liquor.

Similarly to the third alkali-containing solution, said first alkali-containing aqueous solution is preferably an aqueous solution of KOH or NaOH.

For ease of description, reference is made below to the use of NaOH for said alkali-containing solutions. The embodiments described below with reference to a solution of NaOH are also applicable to a solution of KOH or another.

Preferably, said first alkali-containing solution is at least partially formed by the second alkali-containing solution from the decomposition step (e). More preferably, said first alkali-containing solution is entirely, or substantially entirely, formed by at least a portion of said second alkali-containing aqueous solution and no solution of make-up is required.

Said mother liquor contains by-products, e.g. residual poly-condensates and OATs, residual dissolved melamine and NaOH. In particular, the sodium hydroxide is present as free NaOH or in the form of salts, e.g. sodium salts of OATs or sodium carbonates.

At least a first portion of said mother liquor is subjected to the above mentioned step (d), during which said by-products are at least partially hydrolysed into $CO_2$ and $NH_3$. According to particularly preferred embodiments, a second portion of mother liquor is recycled back to said step (a2) and/or step (a1) when quenching is carried out in the presence of alkali.

Preferably said step (d) is a thermal treatment. Preferably said thermal treatment is carried out at temperature of 200 to 300° C. and pressure of 30 to 100 bar.

The carbon dioxide obtained from the by-product hydrolysis at least partially reacts with free NaOH present in the mother liquor to give carbonates and bicarbonates, according to the following reactions:

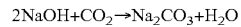

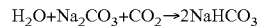

Therefore, an aqueous solution containing $CO_2$ in the form of carbonates and bicarbonates is separated. Preferably, said water stream contains a total amount of $Na_2CO_3$ and $NaHCO_3$ within the range 0.1 to 10% by weight, more preferably between 1.5 to 3.5% by weight.

Preferably, a further portion of carbon dioxide reacts with ammonia, thus providing ammonium carbonate as a separate solution with respect to the above mentioned aqueous solution containing sodium carbonates and bicarbonates. Said ammonia is obtained by the by-product hydrolysis taking place during said step (d) and possibly from the aqueous solution of ammonia provided by the step (b) of stripping.

Carbonates and bicarbonates contained in said aqueous solution are at least partially decomposed back into carbon dioxide and sodium hydroxide, providing the second alkali-containing aqueous solution and a desalinated water stream.

As mentioned above, according to a preferred embodiment, the decomposition of said carbonates and bicarbonates takes place by electrolysis. The electrolysis has several advantages, being carried out at relatively low temperature and with low energy consumption and providing pure or substantially pure products.

Due to the presence in water of (bi)carbonates which involve an alkaline pH higher than 7, the electrolytic process is advantageously carried out in an alkaline electrolytic cell. Typically an alkaline cell comprises two electrodes (i.e. anode and cathode) operating in a liquid alkaline electrolyte solution and said electrodes are separated by a diaphragm. An example of an alkaline cell suitable for the present invention is described in EP 0 212 240.

As stated above, in some embodiments, said aqueous solution containing sodium carbonates and bicarbonates is subjected to an ultrafiltration step before being fed to the electrolysis process, in order to remove suspended solids which may be present therein and would negatively affect the performances of the electrolytic cell.

The second alkali-containing aqueous solution (e.g. sodium hydroxide solution) is obtained from the cathode and the desalinated water stream is obtained from the anode.

At least part of said second alkali-containing aqueous solution is recycled back to at least one of the step (a2) of decomposition, the step (c) of crystallization and the step (a1) of quenching when carried out in the presence of alkali, thus entailing a significant reduction or avoidance of the fresh alkali supply.

In some embodiments, the at least partial recycle of said second alkali-containing solution to at least one of the above steps is carried out upon further concentration of said solution, or of a portion thereof, in a suitable concentration unit.

The desalinated water stream may contain residual amounts of (bi)carbonates. Depending on the residual concentration of (bi)carbonates, said water stream may be at least partially discharged and/or at least partially recycled to the melamine process, thus entailing a significant reduction of the make-up of water. For example, said desalinated water stream may be recycled to the melamine purification process, e.g. to the step (e) and/or to the step (a1).

According to a particularly preferred embodiment, said desalinated water stream does not contain residual (bi) carbonates and is referred to as a stream of clean water. Accordingly, said stream of clean water may be entirely recycled back to the melamine process.

Said process of electrolysis also generates gaseous $CO_2$ and $H_2$, which can be discharged into the atmosphere or stored or used for other purposes. For example, $CO_2$ can be advantageously reused as feed for the synthesis of urea, while $H_2$ can be reused as feed to an ammonia process.

A purification section for carrying out said process and a method of revamping according to the annexed claims are also objects of the present invention.

The revamping of an existing melamine purification section comprises the steps of:

installing a decomposition unit downstream of an existing treatment unit in order to at least partially decompose the (bi)carbonates contained in the aqueous solution leaving the treatment unit into carbon dioxide and alkali, providing an alkali-containing aqueous solution;

installing one or more flow lines in order to at least partially recycle said alkali-containing aqueous solution to at least one of the quencher, the decomposer and the crystallizer.

Said newly-installed decomposition unit is preferably an electrolytic cell.

In some embodiments, said melamine purification section comprises a quencher operating with water or with an aqueous solution of ammonia, and the method of revamping comprises the provision of a quencher operating with an aqueous solution of soluble hydroxides of the alkali metals, preferably of sodium or potassium. This can be made by modification of the existing quencher or installation of a new quencher. Said newly installed quencher advantageously replaces the existing one.

The present invention has the combined advantage of reducing or even preventing the need of alkali and water make-up and decreasing the concentration of (bi)carbonates in the treated waste water.

A first advantage is represented by a significant reduction of the environmental impact. As a matter of fact, a desalinated water stream with a low content of carbonates and bicarbonates is discharged, which is particularly advantageous in case of stringent limitations on the (bi)carbonates concentration in water. Even more advantageously, said desalinated water stream may contain no (bi)carbonates, which results in the provision of clean water.

A second advantages consists in the fact that said desalinated water stream can be recycled to the melamine process, reducing or preventing the need for water make-up. This is a significant advantage because allows reducing the supply of fresh water, which is not always available and entails elevated costs.

A third advantage is that the alkali are advantageously recovered from the effluent of the treatment unit and continuously recirculated within the melamine purification section, reducing or preventing the need for alkali make-up to the decomposer and/or the crystallizer and/or the quencher (when operating in the presence of alkali).

The advantages will emerge even more clearly with the aid of the detailed description below relating to preferred embodiments.

DETAILED DESCRIPTION OF PREFERRED EMBODIMENTS

Figure 1:
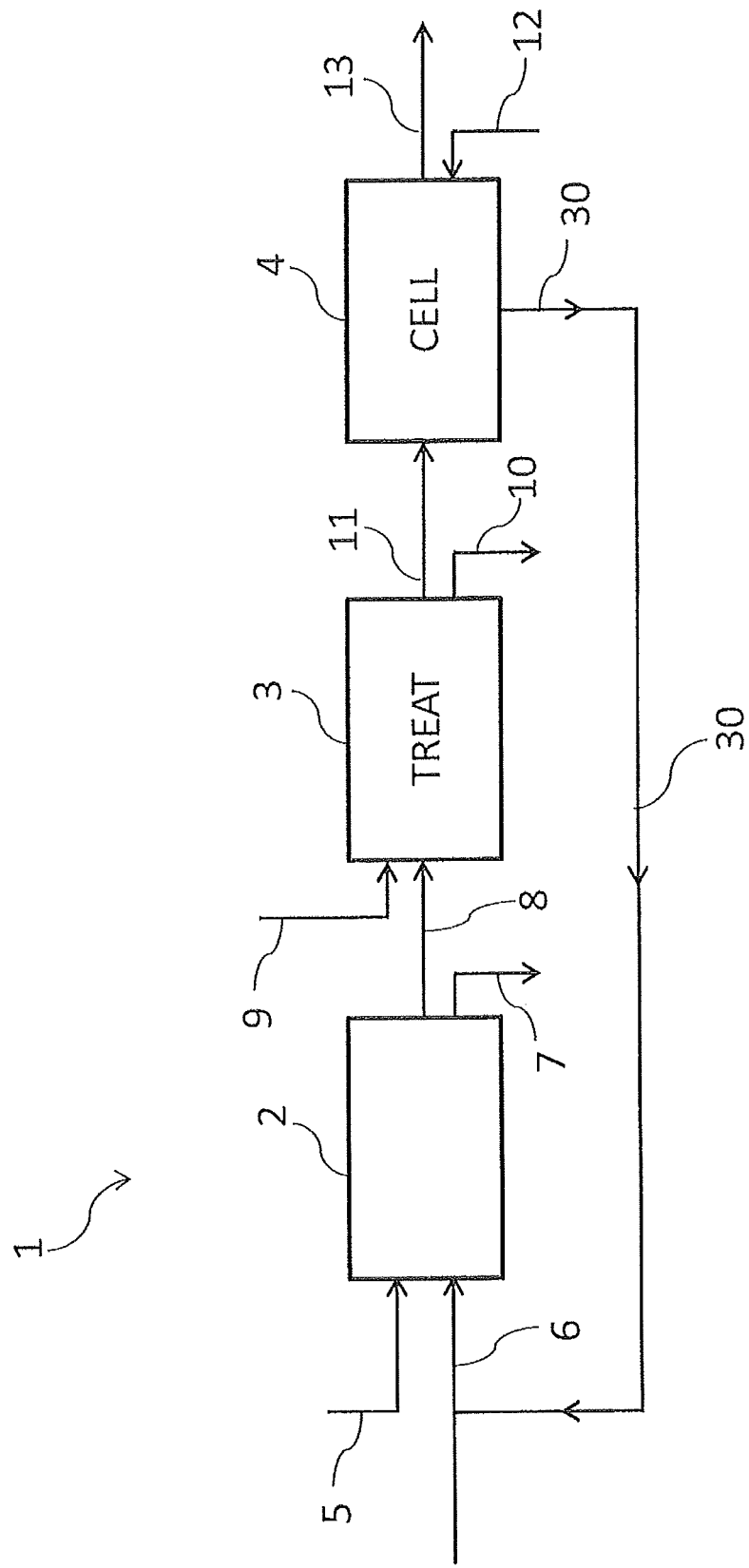
FIG. 1 is a simplified scheme of a melamine purification process according to the invention.

FIG. 1 shows a simplified block scheme of a melamine purification section 1.

Said section 1 comprises a first block 2 essentially including a quencher, a decomposer, a stripper and a crystallizer; a treatment unit 3 and an electrolytic cell 4.

Said block 2 receives a first input stream 5 and a second input stream 6. Said first stream 5 is a melamine melt produced from the high pressure synthesis section (not shown) of a melamine plant and said second stream 6 is an aqueous solution of sodium hydroxide. A portion 30 of said second input stream 6 is provided by the electrolytic cell 4.

Figure 2:
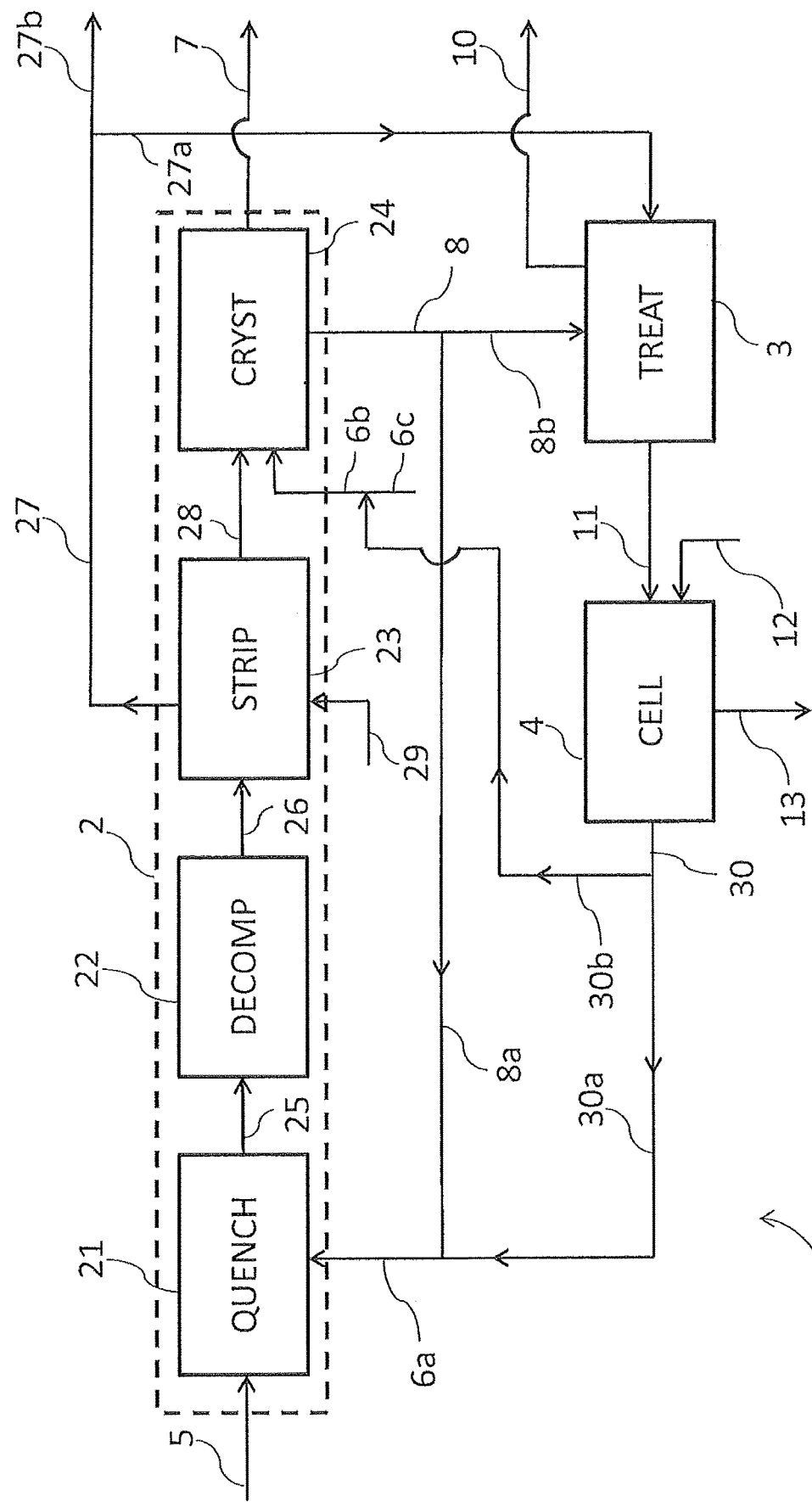
FIGS. 2 to 5 are block schemes of melamine purification processes according to various embodiments of the invention.

As shown in the example of FIG. 2, said second stream 6 consists of an input stream 6a to the quencher and an input stream 6b to the crystallizer. More in particular, a portion 30a of the stream 6a and a portion 30b of the stream 6b are provided by the electrolytic cell 4.

Said block 2 provides solid melamine 7 and a mother liquor 8 containing for example poly-condensates, OATs and NaOH.

Said solid melamine 7 is collected and exported from the purification section and said mother liquor 8 is at least partially subjected to a suitable treatment in the treatment unit 3. Said unit 3 is also fed with an ammonia solution 9, which is preferably provided by the stripper contained in the first block 2, and provides an ammonium carbonate stream 10 and an aqueous solution 11 containing sodium carbonates and bicarbonates.

Said stream 10 containing ammonium carbonate is exported and said solution 11 is fed to the electrolytic cell 4. Said electrolytic cell 4 also receives a stream of fresh water 12 and provides an aqueous solution of sodium hydroxide 30 and a desalinated water stream 13. Said solution 30 is recycled back to the first block 2 and said desalinated water stream 13 is at least partially discharged from the purification section 1.

FIG. 2 shows in greater detail the process of FIG. 1.

According to FIG. 2, the melamine purification section 1 essentially comprises a quencher 21, a decomposer 22, a stripper 23 and a crystallizer 24 (which are part of the block 2 of FIG. 1), the treatment unit 3 and the electrolytic cell 4.

The above mentioned melamine melt 5 is fed to the quencher 21 together with the aqueous solution 6a of sodium hydroxide. Said melamine melt 5 contains melamine, unconverted urea, dissolved ammonia and a number of by-products. Said by-products essentially comprise OATs and poly-condensates.

Inside the quencher 21, the melamine, the unconverted urea and the by-products are dissolved, thus providing a first alkaline aqueous solution of melamine 25 containing by-products.

Said solution 25 is subsequently sent to the decomposer 22, wherein the poly-condensates are at least partially hydrolysed into melamine and OATs thanks to the presence of alkali (NaOH) in said solution 25, thus providing a second alkaline aqueous solution of melamine 26.

Said solution 26 is introduced into the stripper 23, wherein ammonia is stripped out thus providing an aqueous solution of ammonia 27 and a stripped solution 28. Steam 29 is generally used as stripping medium.

According to the example of the figure, said aqueous solution of ammonia 27 is split into two portions; a first portion 27a is sent to the treatment unit 3 and a second portion 27b is exported from the purification section 1.

The stripped solution 28 is further purified by e.g. filtration and clarification with activated carbon and subsequently subjected to crystallization within the crystallizer 24, wherein melamine crystals 7 are separated from the melamine mother liquor 8. Said crystallizer 24 is also fed with an aqueous solution 6b containing sodium hydroxide. According to the example of the figure, said solution 6b is formed by a portion 30b of the alkali-containing solution provided from the electrolytic cell 4 and by a portion 6c of make-up. According to even preferred embodiments, said solution 6b is entirely formed by the portion 30b of the alkali-containing solution from the cell 4, while the portion 6c of make-up is not needed.

A first portion 8a of said mother liquor is mixed with an aqueous solution 30a of sodium hydroxide provided from the electrolytic cell 4 to form the input stream 6a to the quencher 21, as better explained below.

A second portion 8b of said mother liquor is subjected to a high temperature and high pressure treatment in the unit 3 wherein by-products contained in the mother liquor 8 are hydrolysed into CO2 and NH3, providing the sodium (bi) carbonates-containing aqueous solution 11 and the ammonium carbonate solution 10. More in detail, a part of the so obtained CO2 reacts in the unit 3 with the sodium hydroxide contained in the liquor 8 to form sodium carbonates ($Na_2CO_3$) and sodium bicarbonates ($NaHCO_3$). Part of the CO2 also reacts with NH3 to form ammonium carbonate (($NH_4)_2CO_3$). Said NH3 is both provided by the by-product hydrolysis and by the portion 27a of the aqueous solution of ammonia.

The sodium (bi)carbonates-containing aqueous solution 11 is then provided to the alkaline electrolytic cell 4, which is further fed with a stream of fresh water 12.

Within said cell 4, sodium carbonates and bicarbonates contained in the solution 11 are decomposed into CO2 and NaOH to form the aqueous solution of sodium hydroxide 30 and the desalinated water stream 13.

Said solution 30 is partly recycled back to the quencher 21 and partly to the crystallizer 24, while said desalinated water stream 13 is at least partially discharged from the purification section 1.

FIG. 2 illustrates an embodiment wherein the solution 30 is split into two portions 30a and 30b: the portion 30a is directly recycled to the quencher 21 upon mixing with the first portion 8a of the mother liquor thus forming the input stream 6a, and the portion 30b is directly recycled to the crystallizer 24 upon mixing with an optional alkali solution 6c of make-up thus forming the input stream 6b.

Figure 3:
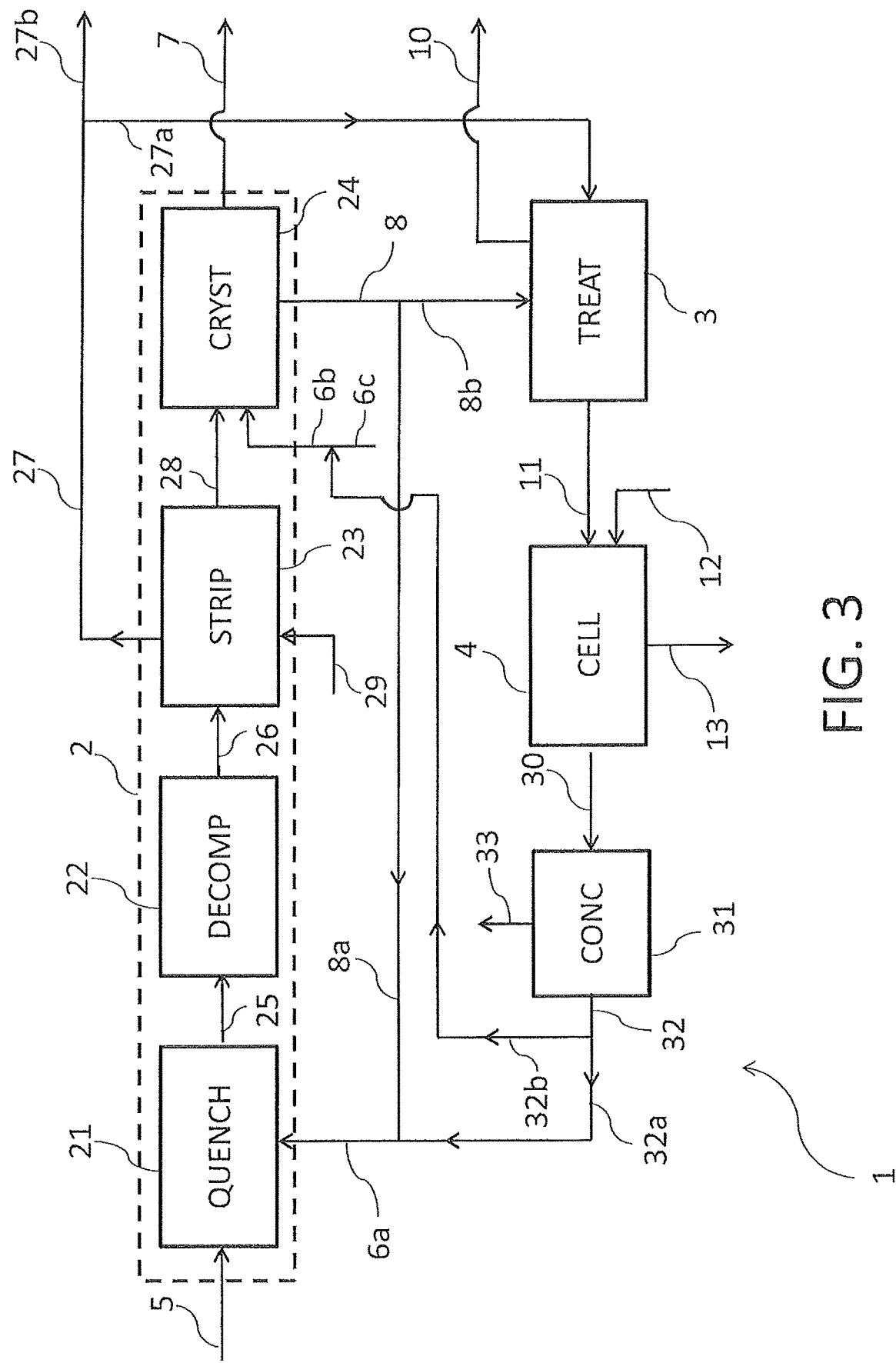
Figure 4:
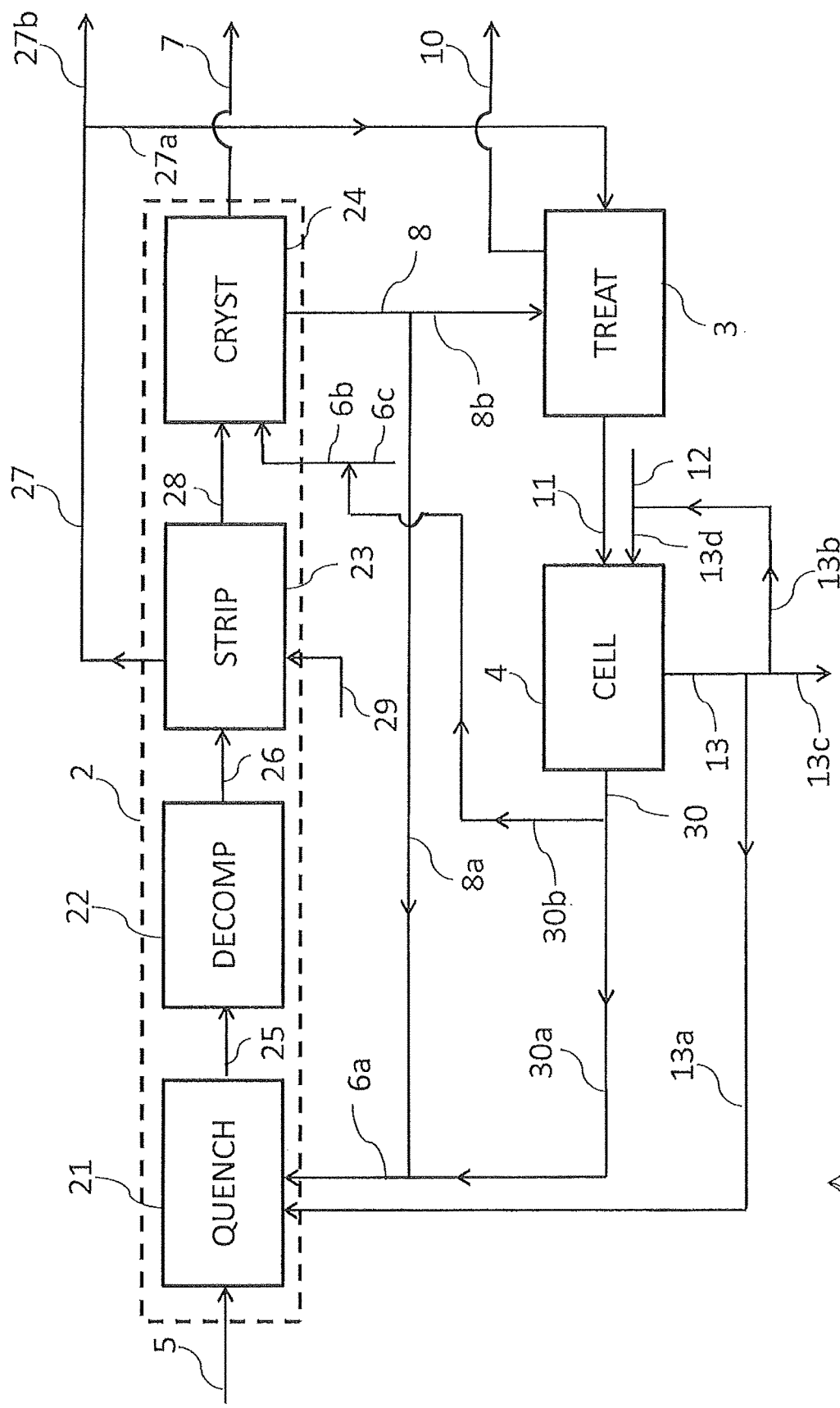
Figure 5:
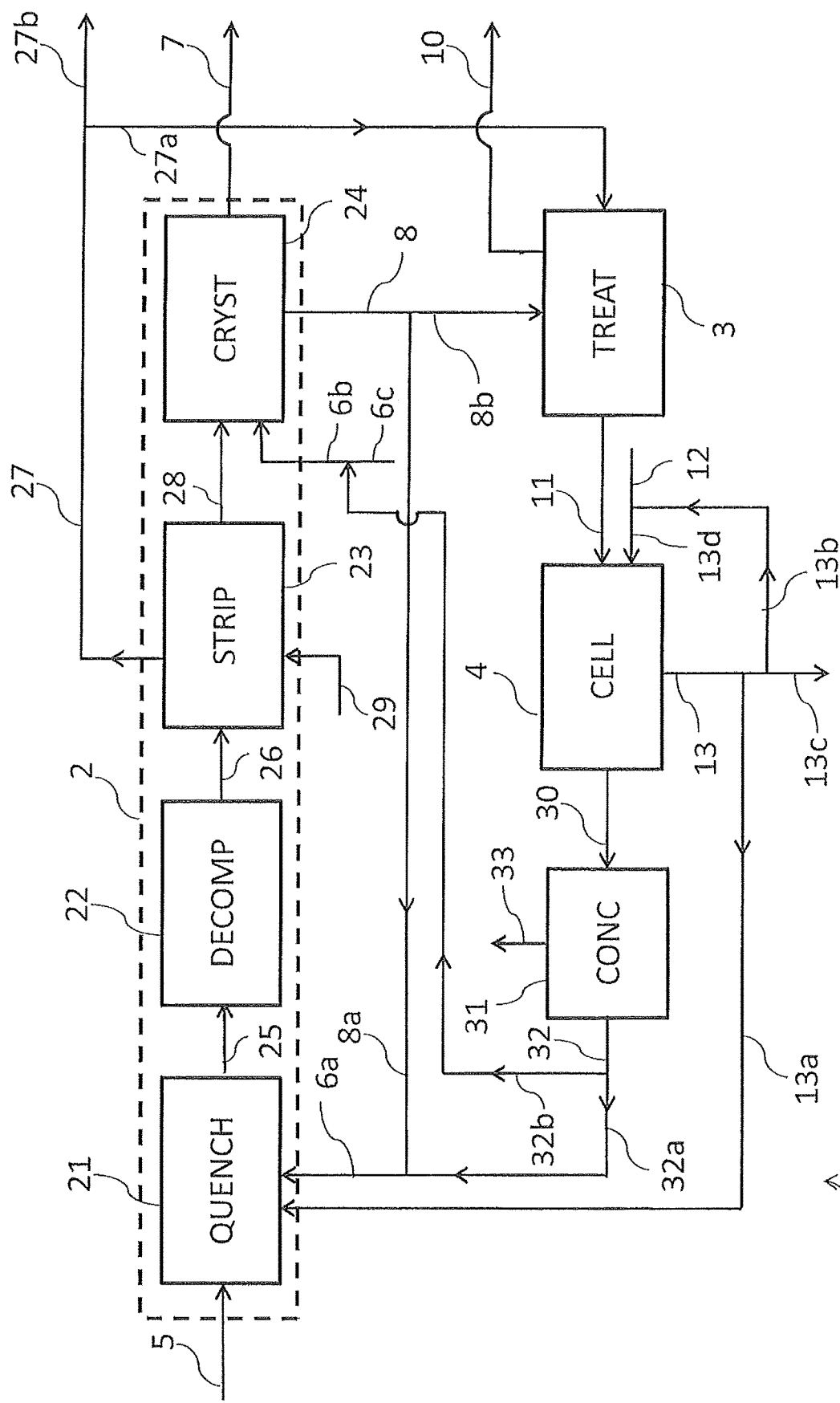

Further embodiments are illustrated in the FIGS. 3 to 5.

FIG. 3 illustrates an embodiment wherein the sodium hydroxide solution 30 is concentrated in a proper concentration unit 31, which provides a concentrated solution 32. Said solution 32 is split into a first portion 32a and a second portion 32b; the first portion 32a is mixed with the portion 8a of the mother liquor and recycled to the quencher 21 and the second portion 32b is mixed with an optional alkali solution 6c of make-up and recycled to the crystallizer 24. Said concentration unit 31 releases a steam flow 33 which can be recycled to a plant steam system.

FIG. 4 illustrates an embodiment wherein the desalinated water stream 13 leaving the electrolytic cell 4 is split into three portions: a first portion 13a is recycled back to the quencher 21, a second portion 13b is joint with fresh water 12 to provide stream 13d which is recycled to the electrolytic cell 4, a third portion 13c is discharged.

FIG. 5 illustrates an embodiment which is a combination of FIGS. 3 and 4, wherein the sodium hydroxide solution 30 is concentrated in the unit 31 before being recycled to the quencher 21 and the crystallizer 24 and the desalinated water stream 13 is split into three portions 13a, 13b, 13c as in the process of FIG. 4.

Figure 6:
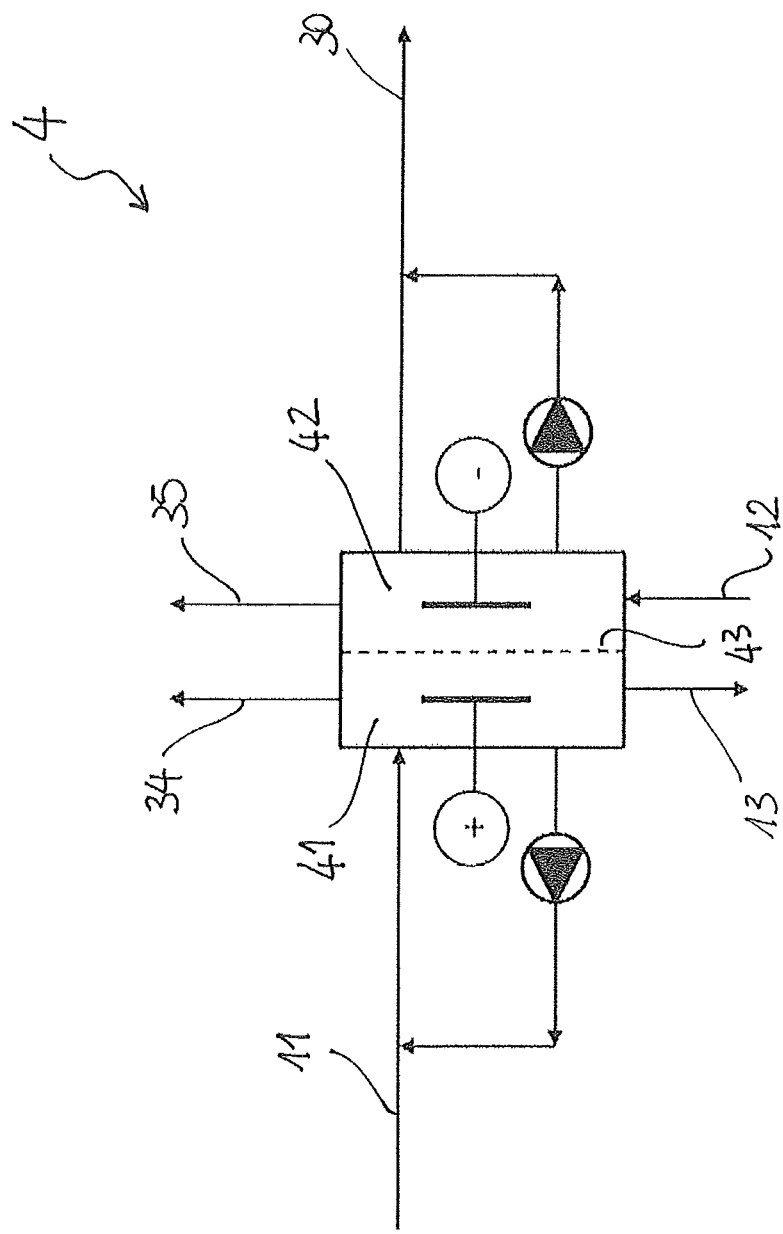
FIG. 6 is a schematic representation of the operation of an alkaline electrolytic cell.

FIG. 6 schematically shows an alkaline electrolytic cell 4, which comprises an anodic compartment 41 and a cathodic compartment 42. Said compartments are separated by a diaphragm 43.

The aqueous solution 11 containing sodium carbonates and bicarbonates is fed to the anodic compartment 41 of the cell 4, while the stream of fresh water 12 is fed to the cathodic compartment 42. The global reactions taking place within the cell 4 are the following:

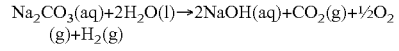

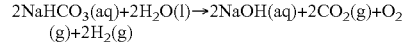

Oxygen and carbon dioxide are released from the anodic compartment 41 as stream 34; cations (i.e. $H_3O^+$ and $Na^+$) migrate to the cathodic compartment 42 forming sodium hydroxide and hydrogen, the former being separated as stream 30 and the latter being extracted as stream 35.

As a result, the aqueous solution of sodium hydroxide 30 is provided by said cathodic compartment 42, while the desalinated water stream 13 is provided by said anodic compartments 41.

What is claimed is:

1. A process for the purification of a melamine melt containing melamine and by-products and obtained from a high pressure non-catalytic synthesis process, said process comprising the steps of:
   (a1) quenching of said melamine melt;
   (a2) decomposition with alkali of at least part of said by-products, providing an alkaline aqueous solution of melamine;

(b) stripping of said alkaline aqueous solution of melamine, resulting in a stripped melamine solution;
(c) crystallization of melamine from said stripped melamine solution with a first alkali-containing aqueous solution and separation of melamine from a mother liquor;
(d) treatment of at least part of said mother liquor, providing an aqueous solution containing carbonates;
(e) decomposition of at least part of the carbonates contained in said aqueous solution into carbon dioxide and alkali, providing a second alkali-containing aqueous solution separated from a water stream;
(f) recycle of at least part of said second alkali-containing aqueous solution to at least one of said steps (a1), (a2) and (c).

2. The process according to claim 1, wherein said decomposition step (e) is performed by means of an electrolysis process of said aqueous solution containing carbonates.

3. The process according to claim 2, wherein said aqueous solution containing carbonates is subjected to an ultrafiltration step before being sent to said electrolysis process.

4. The process according to claim 1, wherein the second alkali-containing aqueous solution provided by said decomposition step (e) is at least partially subjected to a concentration step before being recycled to at least one of said steps (a1), (a2) and (c).

5. The process according to claim 1, at least a portion of said second alkali-containing aqueous solution being recycled to said step (c), wherein said first alkali-containing aqueous solution (6b) is entirely or substantially entirely formed by said at least a portion of the second alkali-containing aqueous solution.

6. The process according to claim 1, wherein said step (a1) of quenching is carried out in the presence of alkali and a third alkali-containing aqueous solution is fed to said step (a1) as a quenching medium.

7. The process according to claim 6, wherein said third alkali-containing aqueous solution comprises a portion of said mother liquor provided from said step (c) of crystallization.

8. The process according to claim 7, wherein said portion of the mother liquor and at least a portion of said second alkali-containing aqueous solution are mixed to form said third alkali-containing aqueous solution or a portion thereof.

9. The process according to claim 1, wherein said alkali-containing solutions are sodium or potassium hydroxide solutions.

10. The process according to claim 1, wherein said water stream is at least partially recycled back to a melamine plant.

* * * * *